US00PP11203P

United States Patent [19]

VandenBerg

[11] Patent Number: Plant 11,203

[45] Date of Patent: Feb. 1, 2000

[54] CHRYSANTHEMUM PLANT NAMED 'YOLOMPOC'

[75] Inventor: Cornelis P. VandenBerg, Salinas, Calif.

[73] Assignee: Yoder Brothers, Inc., Barberton, Ohio

[21] Appl. No.: 09/112,649

[22] Filed: Jul. 9, 1998

[51] Int. Cl.[7] ..... A01H 5/00

[52] U.S. Cl. ..... Plt./286

[58] Field of Search ..... Plt./286, 297

[56] References Cited

U.S. PATENT DOCUMENTS

P.P. 5,660 2/1986 Duffett ..... Plt./286
P.P. 8,292 7/1993 Vandenberg ..... Plt./286
P.P. 10,680 11/1998 Vandenberg ..... Plt./286

*Primary Examiner*—Howard J. Locker
*Attorney, Agent, or Firm*—C. A. Whealy

[57] ABSTRACT

A distinct cultivar of Chrysanthemum plant named 'Yolompoc', characterized by its uniformly mounded plant habit; freely branching habit giving a full and dense appearance; uniform and early flowering; numerous inflorescences per plant; large daisy spray-type inflorescences that are about 7.5 cm in diameter; red purple ray florets with bright yellow disc florets; and good postproduction longevity with inflorescences and leaves maintaining good substance and color for about three or four weeks in an interior environment.

2 Drawing Sheets

BACKGROUND OF THE INVENTION

The present invention relates to a new and distinct cultivar of Chrysanthemum plant, botanically known as *Dendranthema grandiflora* and hereinafter referred to by the cultivar name Yolompoc. The plant is being marketed under the name Lompoc.

The new Chrysanthemum is a product of a planned breeding program conducted by the inventor in Salinas, Calif. The objective of the breeding program is to create new pot-type Chrysanthemum cultivars having desirable inflorescence forms and floret colors and excellent post-production longevity.

The new Chrysanthemum originated from a cross made by the breeder in July, 1993, in Salinas, Calif., of the commercial Chrysanthemum cultivar Akron (disclosed in U.S. Plant Pat. No. 9,105) as the male, or pollen, parent with an unnamed proprietary Chrysanthemum seedling selection as the female, or seed, parent.

The new Chrysanthemum was discovered and selected by the inventor as a flowering plant within the progeny of the stated cross in a controlled environment in Salinas, Calif., in April, 1994. The selection of this plant was based on its desirable inflorescence form and floret colors and good post-production longevity.

Asexual reproduction of the new Chrysanthemum by terminal cuttings harvested in a controlled environment in Salinas, Calif., has shown that the unique features of this new Chrysanthemum are stable and reproduced true to type in successive generations.

SUMMARY OF THE INVENTION

The cultivar Yolompoc has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yolompoc'. These characteristics in combination distinguish 'Yolompoc' as a new and distinct Chrysanthemum:

1. Uniformly mounded plant habit.

2. Freely branching habit, very full and dense.
3. Uniform and early flowering.
4. Floriferous with numerous inflorescences per plant.
5. Large daisy spray-type inflorescences that are about 7.5 cm in diameter.
6. Red purple florets with bright yellow disc florets.
7. Good postproduction longevity with inflorescences and leaves maintaining good substance and color for about three or four weeks in an interior environment.

The new Chrysanthemum is similar in ray floret color to the parent cultivar Akron. However in side-by-side comparisons in Salinas, Calif., under commercial practice, plants of the new Chrysanthemum differed from plants of the cultivar Akron in the following characteristics:

1. Plants of the new Chrysanthemum are taller than plants of the cultivar Akron.
2. Plants of the new Chrysanthemum are more freely branching and therefore denser than plants of the cultivar Akron.
3. Plants of the new Chrysanthemum have a fewer but wider ray florets than plants of the cultivar Akron.
4. Ray florets of plants of the new Chrysanthemum maintain their color better than ray florets of plants of the cultivar Akron.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type.

The photograph on the first sheet comprises a top perspective view of a typical flowering plant of 'Yolompoc'.

The photograph at the top of the second sheet is a close-up view of typical inflorescences of plants of 'Yolompoc'.

The photograph at the bottom of the second sheet is a close-up view of upper and lower surfaces of typical inflorescences (top) and typical leaves (bottom) of plants of 'Yolompoc'. Floret and foliage colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Leamington, Ontario, Canada, and Salinas, Calif., under greenhouse conditions which approximate those generally used in commercial potted Chrysanthemum production. Four unrooted cuttings were directly stuck in a 15-cm container and pinched once. Measurements and numerical values represent averages of typical flowering plants.

Botanical classification: *Dendranthema grandiflora* cultivar Yolompoc.

Commercial classification: Daisy spray-type pot Chrysanthemum.

Parentage:

*Male or pollen parent.*—*Dendranthema grandiflora* cultivar Akron, disclosed in U.S. Plant Pat. No. 9,105.

*Female or seed parent.*—Unnamed proprietary *Dendranthema grandiflora* seedling selection.

Propagation:

*Type.*—Terminal tip cuttings.

*Time to rooting.*—Seven to ten days with soil temperartures of 21° C.

*Rooting habit.*—Fine, fibrous and well-branched.

Plant description:

*Appearance.*—Perennial herbaceous daisy spray-type pot Chrysanthemum. Inverted triangle. Stems initially upright, then somewhat spreading giving a uniformly mounded appearance to the plant. Very freely branching; about five lateral branches develop after removal of terminal apex (pinching), very dense and full plants.

*Plant height.*—About 24 cm.

*Plant width.*—About 34 cm.

*Foliage description.*—Arrangement: Alternate. Length: About 7 cm. Width: About 5 cm. Apex: Cuspidate to mucronate. Base: Attenuate. Margin: Palmately lobed, sinuses between lateral lobes parallel. Texture: Upper and lower surfaces with very fine pubescence. Veins prominent on lower surface. Petiole length: About 2 cm Color: Young foliage upper surface: 147A. Young foliage lower surface: Darker than 147B. Mature foliage upper surface: Darker than 147A. Mature foliage lower surface: Darker than 147B. Venation upper surface: 147A. Venation lower surface: 147B.

INFLORESCENCE DESCRIPTION:

*Appearance.*—Daisy spray-type inflorescence form with oblong-shaped ray florets. Inflorescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about eight weeks later.

*Postproduction longevity.*—Inflorescenses and leaves will maintain good color and substance for about three or four weeks in an interior environment.

*Quantity of inflorescenses.*—Floriferous; about six inflorescences per terminal with about 30 inflorescences per plant.

*Inflorescence bud.*—Height: About 5 mm. Diameter: About 6 mm. Color: Greener and darker than 144A.

*Inflorescence size.*—Diameter: About 7.5 cm. Depth (height): About 1.2 cm. Diameter of disc: About 1.5 cm.

*Ray florets.*—Shape: Oblong with short corolla tube. Aspect: Straight, mostly flat. Orientation: Slightly upright. Length: About 3.8 cm. Width: About 1.2 cm. Apex: Rounded. Margin: Entire. Texture: Smooth, glabrous. Number of ray florets per inflorescence: About 21. Color: When opening, upper surface: 61A. When opening, lower surface: 61A. Fully opened, upper surface: Close to 61A. Fully opened, lower surface: Close to 61A and streaked with 77B to 77C to 77D.

*Disc florets.*—Shape: Tubular. Apex: Serrated. Length: About 7 mm. Width: Apex: About 2 mm. Base: About 1 mm. Number of disc florets per inflorescence: Numerous, about 131. Color: Immature: 154A. Mature: Apex: 9A. Mid-section: 154A. Base: White, 155D.

*Peduncle.*—Aspect: Flexible, strong, angled about 45° to stem. Length, first peduncle: About 2.7 cm. Length, fourth peduncle: About 4.3 cm. Texture: Pubescent. Color: Greener than 144A.

*Reproductive organs.*—Androecium: Present on disc florets only. Anther color: 9A. Pollen amount: Moderate. Pollen color: 9A. Gynoecium: Present on both ray and disc florets.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named 'Yolompoc', as illustrated and described.

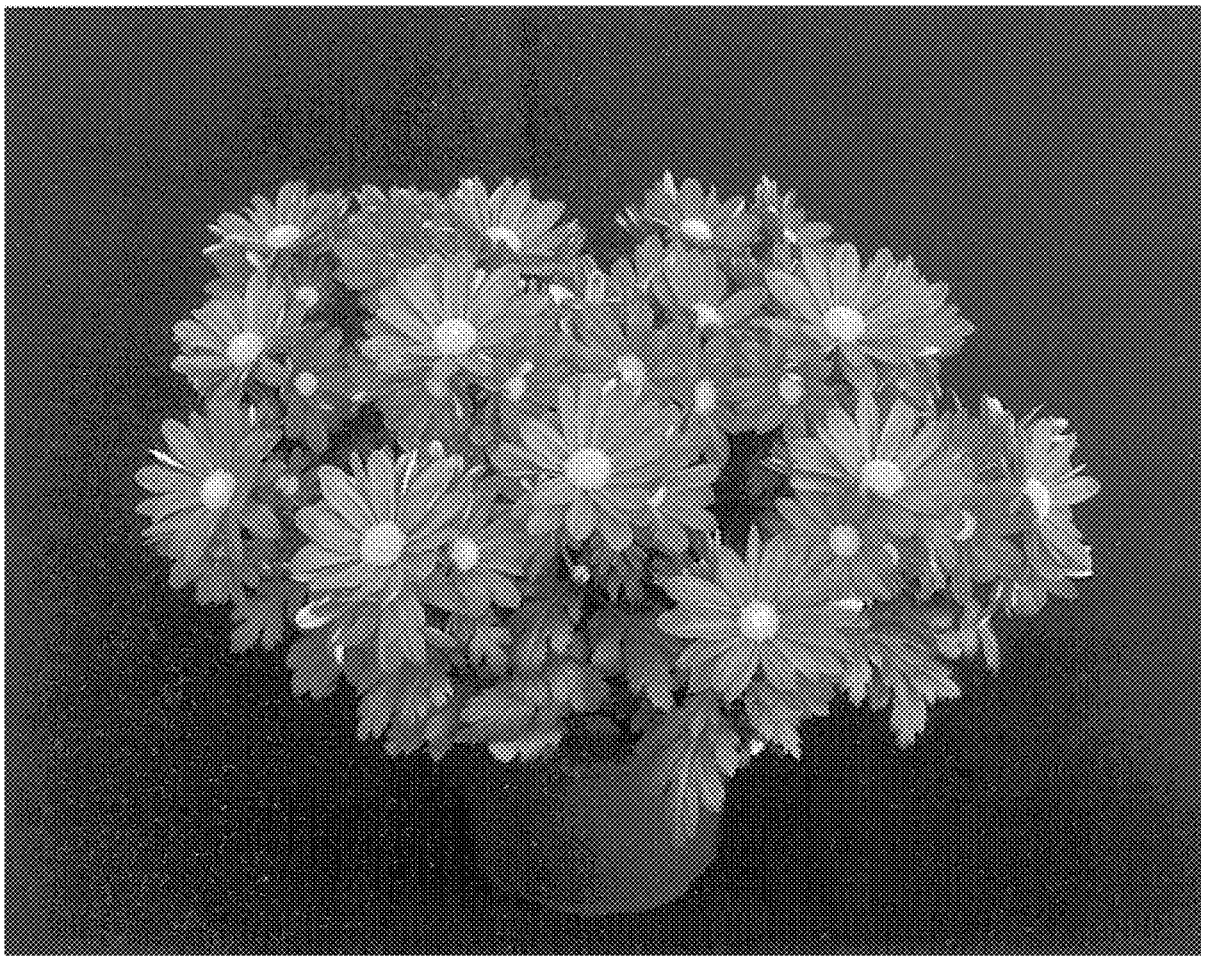

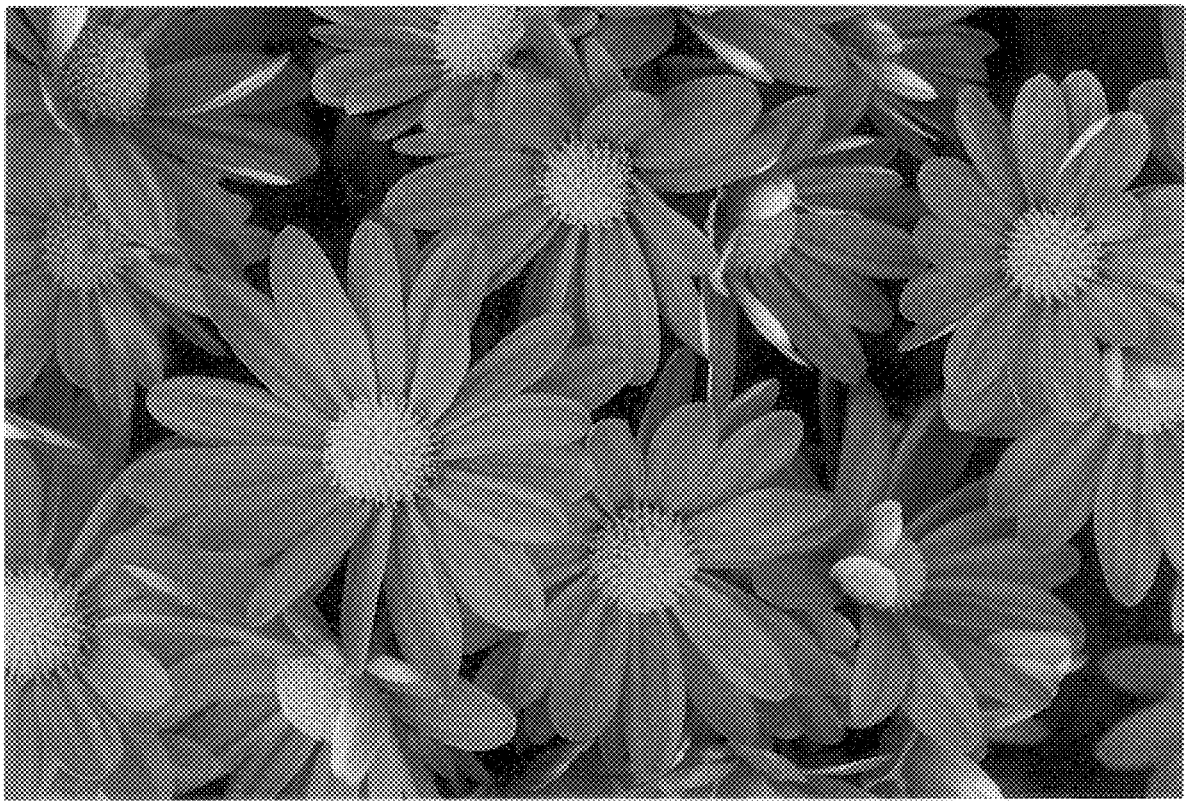
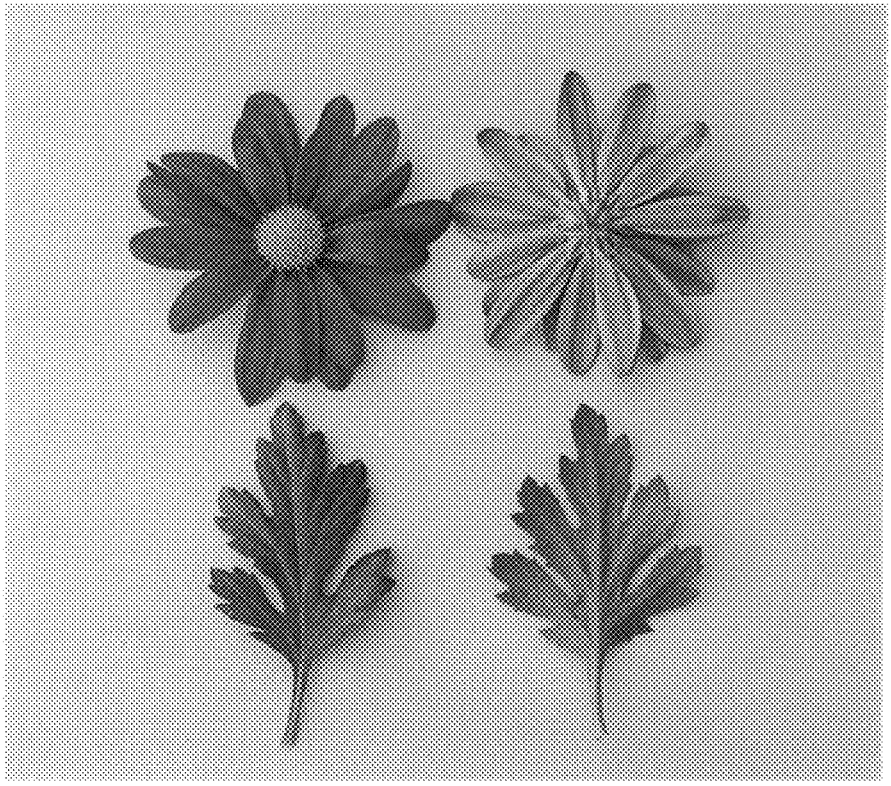

* * * * *